United States Patent [19]
Ishikawa et al.

[11] Patent Number: 5,985,924
[45] Date of Patent: Nov. 16, 1999

[54] METASTASIS SUPPRESSORY AGENTS

[75] Inventors: Hiromichi Ishikawa; Tomoko Watanabe; Satoshi Nishimuro, all of Kobe; Mitsuru Hirota, Minowamura, all of Japan

[73] Assignee: JCR Pharmaceuticals Co., Ltd., Hyogo, Japan

[21] Appl. No.: 08/749,403

[22] Filed: Nov. 15, 1996

[30] Foreign Application Priority Data

Nov. 16, 1995 [JP] Japan ................................. 7-323710

[51] Int. Cl.⁶ .................................................. A61K 31/19
[52] U.S. Cl. ............................................................ 514/557
[58] Field of Search ............................................. 514/557

[56] References Cited

FOREIGN PATENT DOCUMENTS

| 7048250 A2 | 2/1995 | Japan | 515/557 |
| 94 05152 | of 0000 | WIPO . | |
| 95 04526 | 2/1995 | WIPO . | |

OTHER PUBLICATIONS

Cancer Letters, Vol. 94, No. 2, 1995, pp. 213–218, Kyung-–Hee Sohn et al., "Anti–angiogenic activity of triterpene acids".

Br. J. of Cancer, Vol, 72, No. 2, Oct. 1995, pp. 257–267. CT Baillie et al., "Tumour vasculature —a potential therapeutic target".

Ann. N.Y. Acad. Science Vol. 732, Sep. 6, 1994, pp. 263–272, Eric P. Sipos et al., "Inhibition of Tumor Angiogenesis".

*Primary Examiner*—Jerome D. Goldberg
*Attorney, Agent, or Firm*—Jacobson, Price, Holman & Stern, PLLC

[57] ABSTRACT

The present invention provides novel metastasis suppressory agents with a lowered degree of toxicity, comprising ursolic acid or its salt as an active ingredient, which can be administered to patients per os or through injection, thus enabling the patients to receive post-operative ambulatory treatment.

11 Claims, No Drawings

METASTASIS SUPPRESSORY AGENTS

The present invention relates to metastasis suppressory agents which show reduced side effects.

BACKGROUND OF THE INVENTION

One of the greatest difficulties encountered in the surgical therapies of cancers is the post-operative recurrence. In many cases, metastasis is the primary cause of such recurrence. Metastasis involves a series of complex reactions, inclusive of separation of cancer cells from the primary nidus, followed by infiltration into the surrounding tissues, and proliferation at distant sites of the body to thereby form the secondary, metastasized nidi.

Cancer cells, even after separation from the primary nidus, are hindered from further spreading by the nearby existing extracellular matrix composed of sugar proteins, such as various collagens, fibronectins and laminins, proteoglycans, etc. Cancer cells, on the other hand, cleave and degrade the extracellular matrix structure and migrate, while taking full advantage of a variety of proteases and glycosidases secreted by themselves or the interstitium cells.

Cancer cells having separated in this manner from the primary nidus invade the vasculature, then travel to distant organs, infiltrate into the basement membrane of vascular endothelia and finally lodge in distant tissues for proliferation.

Consequently, suppression of metastasis bears great importance as a one of cancer therapies. For the purpose of this, there have so far been developed various metastasis suppressory agents, such as platelet aggregation suppressory agents, matrix metalloproteinase inhibitors and adhesion-factor suppressory agents. Nevertheless, these have not turned out to provide any effective means for suppressing metastasis.

SUMMARY OF THE INVENTION

The present invention intends to have as its object to provide metastasis suppressory agents which contain as an active ingredient a compound being free from any side effects and exhibiting an increased degree of safety and highly efficacious metastasis suppressory activity, as has not been the case with the conventionally known chemotherapy drugs.

The present inventors, from the standpoint of securement of enhanced safety, took notice of physiological activities manifested by naturally occurring compounds contained in edible plants, and had been conducted extensive research and investigation while seeking for a compound which even after oral administration elicits suppressory activity against metastasis. As a result, it was discovered that ursolic acid represented by the below-shown chemical formula, which is widely distributed in various species of plants, such as apple, persimmon and pear. can suppress metastasis by either of the oral and intravenous administration methods, and this finding, followed by further accumulated research, has resulted into completion of the present invention:

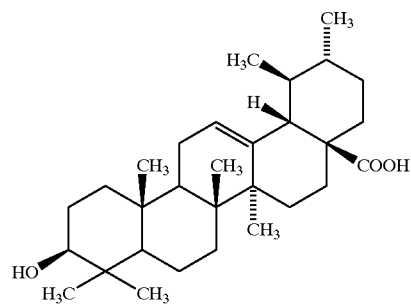

The present invention is concerned with metastasis suppressory agents which comprise ursolic acid or its salt as an active ingredient.

DETAILED DESCRIPTION

Ursolic acid may be in the form of either free acid or pharmaceutically acceptable salt, such as sodium and potassium salts.

Ursolic acid or its salt can be administered to adult patients at a daily dose in the range of 10 mg to 3,000 mg, preferably about 500 mg, per os, or parenterally, for example, by such means as injection, if desired.

Ursolic acid or its salt may be administered to patients directly as such or after being processed into a suitable dosage form. Specific examples of such dosage form include pharmaceutical preparations for internal use, such as ordinary powders, granules, tablets, capsules and liquids (inclusive of syrups), and these pharmaceutical preparations can be produced following the conventional procedures by incorporating ursolic acid with conventionally used additives. In the case of pharmaceutical preparations for internal use, employable as such additives are conventionally known ingredients or components for pharmaceutical preparations, such as excipients (e.g., starch and lactose), binders (e.g., celluloses and polyvinyl-pyrrolidone), disintegrating agents (e.g., carboxymethyl-cellulose), lubricants (e.g., magnesium stearate),. coating agents (e.g., hydroxyethylcellulose), flavoring agents, coloring agents, preservatives and emulsifiers.

Ursolic acid belongs to a kind of triterpenes, as represented by the above-illustrated chemical formula and, with its extremely reduced toxicity, can safely be administered to patients, as may be evidenced by the facts that it does not exert any adverse effects on the proliferation of cultured cells in vitro and that it is in wide use as a drug or an emulsifier for food use.

Ursolic acid according to the present invention exhibits satisfactory metastasis suppressory activity, as is evident from the test examples to be described below, and can be used as a metastasis suppressory agent against a variety of cancers, such as malignant melanoma, hysteromyoma, esophageal carcinoma, skin cancer, stomach cancer, pulmonary carcinoma, cancers of the small and large intestines, pancreatic carcinoma, breast cancer and vesical carcinoma, as well as malignant tumors, such as choriocarcinoma, brain tumor, lymphatic sarcoma and leukemia.

The present invention provides metastasis suppressory agents with lowered toxicity which can be administered to patients per os or by injection, namely a new type of drugs with reduced side effects, thus making great contribution to the medical treatment of cancer and the pharmaceutical industry.

Below described are the examples to illustrate the present invention in more detail.

TEST EXAMPLE 1

Effect of Ursolic Acid on the Proliferation of Cultured Cells:

(a) Test Method

Human normal fibroblast cells and B16 F10 malignant melanoma in suspension ($5 \times 10^4$ cells) were cultivated for 2 days, and then for 24 hours in the presence of 0.1 $\mu$M and 1 $\mu$M of ursolic acid and in the absence of the same, respectively. The cells were harvested, and their numbers were counted to determine the effect of ursolic acid on the cell proliferation.

(b) Test results

Shown in Table 1 are the test results, which indicate that ursolic acid did not exert any effect on the proliferation of melanoma cells at concentrations of 1 $\mu$M and 0.1 $\mu$M.

TABLE 1

Effects of ursolic acid on the cultured cells:

| Concn. of ursolic acid (M) | Rate of proliferation (%) | |
|---|---|---|
| | Human fibroblast cell | Malignant melanoma cell |
| 0.1 $\mu$M | 101.3 | 98.4 |
| 1 $\mu$M | 99.5 | 117.7 |

Note: The proliferation rate (%) is expressed in a ratio of a number of proliferated cells treated with ursolic acid against a number of proliferated cells not treated with ursolic acid.

EXAMPLE 1

Pharmaceutical preparations for metastasis suppression were prepared in accordance with the following formulations:

| Preparation for internal use: | |
|---|---|
| Ursolic acid | 300 mg |
| Sodium carboxymethylcellulose | 50 mg |
| Purified water | To make the total to 10 ml |
| Injectable solution: | |
| Ursolic acid | 250 mg |
| Sesame oil | To make the total to 5 ml |

EXAMPLE 2

Test in Mice on the Suppression of Metastasis of Malignant Melanoma;

(a) Test Method

A suspension of B16 F10 malignant melanoma cells was given groups of mice each consisting of 10 animals intravenously. During the period of Days 7 to 13 after injection of melanoma cells, the oral preparation containing ursolic acid was administered to mice orally once a day, while the injectable solution was applied to animals intraperitoneally once a day, and the lungs were removed on Days 14 to examine each group for a number of metastasized nidi having lodged in the lungs. The same test was carried out with oleanolic acid as represented by the following chemical formula which has the 29-position methyl group of ursolic acid in a different position and which also belongs to the same five-ring triterpenes as ursolic acid.

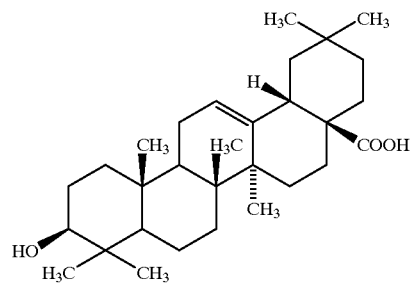

(b) Test Results

Tabulated in Table 2 are the results of the above test, which reveal that ursolic acid, after intraperitoneal and oral administration, reduced significantly the metastasis in the lungs of melanoma cells, as compared with the control group not treated through administration of ursolic acid.

On the other hand, oleanolic acid, even when dosed at 300 mg/kg, did not exhibit significant suppression of metastasis.

TABLE 2

Results of suppression of metastasis by ursolic acid

| Drug substance | Dose (mg/kg) | Route of administration | Rate of metastasis suppression (%) |
|---|---|---|---|
| Control | — | — | 0 |
| Ursolic acid | 100 | Intraperitoneal | 66.2** |
| Ursolic acid | 100 | peros | 58.7* |
| (Oleanolic acid | 300 | peros | 14.5) |

Note: A test of significance;
*, $p < 0.10$ against control group.
**, $p < 0.05$ against control group

We claim:

1. A method for suppressing metastasis comprising administering an effective amount of ursolic acid or its salt as active ingredient in commbination with a pharmacoloically acceptable carrier to a patient in need thereof.

2. The method of claim 1, wherein the amount of ursolic acid is 10–3000 mg/day.

3. The method of claim 1, wherein the amount of ursolic acid is 250–3000 mg/day.

4. The method of claim 1, wherein the amount of ursolic acid is 500–3000 mg/day.

5. The method of claim 3, wherein the agent is administered by injection.

6. The method of claim 4, wherein the agent is administered orally.

7. A method for suppressing metastasis comprising administering to a patient in need thereof an effective amount of ursolic acid, or a salt thereof.

8. The method of claim 7, wherein the amount of ursolic acid is 250–3000 mg/day.

9. The method of claim 7, wherein the amount of ursolic acid is 500–3000 mg/day.

10. The method of claim 7, wherein the ursolic acid is administered by injection.

11. The method of claim 7, wherein the ursolic acid is administered orally.

* * * * *